United States Patent [19]

Haddad

[11] Patent Number: 5,053,211
[45] Date of Patent: Oct. 1, 1991

[54] MANUFACTURE OF AMS-18 CRYSTALLINE BOROSILICATE MOLECULAR SIEVE

[75] Inventor: Muin S. Haddad, Naperville, Ill.

[73] Assignee: Amoco Corporation, Chicago, Ill.

[21] Appl. No.: 62,247

[22] Filed: Jun. 15, 1987

Related U.S. Application Data

[63] Continuation of Ser. No. 909,638, Sep. 19, 1986, abandoned, which is a continuation of Ser. No. 834,606, Feb. 28, 1986, abandoned, which is a continuation of Ser. No. 543,977, Oct. 20, 1983, abandoned, which is a continuation of Ser. No. 386,285, Jun. 8, 1982, abandoned, which is a continuation-in-part of Ser. No. 279,207, Jun. 30, 1981, abandoned.

[51] Int. Cl.$^5$ ............................................. C01B 35/12
[52] U.S. Cl. ..................................... 423/277; 423/328; 208/134
[58] Field of Search ................ 502/202; 423/277, 328; 208/134

[56] References Cited

U.S. PATENT DOCUMENTS

| 4,107,195 | 8/1978 | Rollmann .............................. 423/329 |
| 4,139,600 | 2/1979 | Rollmann et al. ................... 423/329 |
| 4,268,420 | 5/1981 | Klotz .................................... 423/277 |
| 4,285,919 | 8/1981 | Klotz .................................... 423/277 |
| 4,331,641 | 5/1982 | Hinnenkamp et al. .............. 423/277 |
| 4,456,582 | 6/1984 | Marosi et al. ........................ 423/277 |
| 4,656,016 | 4/1987 | Taromasso et al. ................. 423/277 |

FOREIGN PATENT DOCUMENTS 2024790 1/1980 United Kingdom ................ 423/277

OTHER PUBLICATIONS

Taronasso et al., "Proceedings of the 5th Conference on Zeolites", Jun. 2-6, 1980, pp. 1-8.
DuPont, "Ludox ® Colloidal Silica Properties, Uses, Storeage and Handling".

Primary Examiner—R. Bruce Breneman
Attorney, Agent, or Firm—Wallace L. Oliver; William H. Magidson; Ralph C. Medhurst

[57] ABSTRACT

AMS-1B crystalline borosilicate molecular sieve is prepared by reacting under crystallization conditions, in substantial absence of a metal or ammonium hydroxide, an aqueous mixture containing an oxide of silicon, an oxide of boron, an alkylammonium cation or a precursor of an alkylammonium cation, and ethylenediamine, and the product formed from such method.

21 Claims, No Drawings

MANUFACTURE OF AMS-1B CRYSTALLINE BOROSILICATE MOLECULAR SIEVE

CROSS REFERENCE TO RELATED APPLICATIONS

This is a continuation of application Ser. No. 909,638, filed Sept. 19, 1986, which in turn is a continuation of Ser. No. 834,606, filed Feb. 28, 1986, which in turn is a continuation of Ser. No. 543,977, filed Oct. 20, 1983, which in turn is a continuation of Ser. No. 386,285, filed June 8, 1982, which in turn is a CIP of Ser. No. 279,207, filed June 30, 1981, all now abandoned.

BACKGROUND OF THE INVENTION

This invention relates to a new method to manufacture molecular sieves and more particularly to a new method to manufacture crystalline borosilicate AMS-1B molecular sieve and to a product made from that method.

Zeolitic materials, both natural and synthetic, are known to have catalytic capabilities for many hydrocarbon processes. Zeolitic materials typically are ordered porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alkaline-earth-metal cations, ammonium ions, or hydrogen ions.

Boron is not considered a replacement for aluminum or silicon in a zeolitic composition. However, recently a new crystalline borosilicate molecular sieve AMS-1B was disclosed in U.S. Pat. Nos. 4,268,420 and 4,269,813 incorporated by reference herein. According to these patents AMS-1B can be synthesized by crystallizing a source of an oxide of silicon, an oxide of boron, an oxide of sodium and an organic template compound such as a tetra-n-propylammonium salt. In order to form a catalytically-active species of AMS-1B, sodium ion typically is removed by one or more exchanges with ammonium ion followed by calcination. Other methods to produce borosilicate molecular sieves include using a combination of sodium hydroxide and aqueous ammonia together with an organic template as disclosed in U.S. Pat. No. 4,285,919, incorporated herein by reference, and using high concentrations of amine such as hexamethylenediamine as described in German Patent Application 28 30 787. British Patent Application 2,024,790 discloses formation of a borosilicate using ethylene diamine with sodium hydroxide. Aluminosilicates have been prepared with low sodium content using diamines containing four or more carbon atoms as described in European Published Patent Applications 669 and 11 362. U.S. Pat. Nos. 4,139,600 and 4,151,189 describe methods to produce aluminosilicate sieves containing low sodium using diamines or $C_2$–$C_5$ alkyl amines.

A method to produce AMS-1B crystalline borosilicate molecular sieve which is low in sodium would be desirable in that an exchange procedure to remove sodium would be unnecessary. Also a method to produce AMS-1B crystalline borosilicate having a higher boron content than usually prepared by conventional techniques would be very advantageous. Further, a method to produce AMS-1B crystalline borosilicate without use of added alkali or ammonium hydroxides would be desirable. In addition a product formed from such method which shows increased activity over conventionally-prepared material would be most advantageous.

SUMMARY OF THE INVENTION

This invention is a method to prepare AMS-1B crystalline borosilicate molecular sieve comprising reacting under crystallization conditions, in substantial absence of a metal or ammonium hydroxide, an aqueous mixture containing an oxide of silicon, an oxide of boron, an alkylammonium cation or a precursor of an alkylammonium cation, and ethylenediamine, and the product formed from such method.

BRIEF DESCRIPTION OF THE INVENTION

Conventionally, AMS-1B borosilicate molecular sieve is prepared by crystallizing an aqueous mixture of an oxide of boron, an oxide of silicon, and an organic template compound in the presence of an alkali metal hydroxide, usually sodium hydroxide. When such a mixture is crystallized, the resulting AMS-1B molecular sieve contains alkali metal, usually sodium, ions to balance the negative framework charge caused by substitution of a boron atom for silicon in the crystalline sieve structure. However, when used for catalytic purposes, presence of sodium ion usually is detrimental. Typically, before a catalytic composition is made, the hydrogen form of AMS-1B is prepared by exchange with ammonium ion followed by drying and calcination. This invention is a method of directly crystallizing AMS-1B molecular sieve having a low sodium content which uses less of expensive alkylammonium template compound than used in conventional preparations.

In another aspect of this invention, AMS-1B crystalline borosilicate can be formed having higher boron contents than usually formed using conventional techniques.

Still another aspect of this invention is the product formed by a method which does not use a metal or ammonium hydroxide and in which AMS-1B crystalline borosilicate is formed from an aqueous mixture containing a low water to silica ratio.

According to this invention, AMS-1B crystalline molecular sieve is formed by crystallizing an aqueous mixture containing sources for an oxide of boron, an oxide of silicon, a tetraalkylammonium compound and ethylenediamine in the substantial absence of a metal or ammonium hydroxide.

Typically, the mole ratios of the various reactants can be varied to produce the crystalline borosilicates of this invention. Specifically, the molar ratio of initial reactant concentration of silica to oxide of boron can range from about 2 to about 400, preferably about 4 to about 150 and most preferably about 5 to about 80. The molar ratio of water to silica can range from about 2 to about 500, preferably about 5 to about 60 and most preferably about 10 to about 35. It has been found that preparation using a water to silica molar ratio of about 10 to about 15 can be especially preferable. The molar ratio of ethylenediamine to silicon oxide used in the preparation of AMS-1B crystalline borosilicate according to this invention should be above about 0.05, typically below about 5, preferably about 0.1 to about 1.0, and most preferably about 0.2 to about 0.5. The molar ratio of alkylammonium template compound or precursor to silicon oxide useful in the preparation of this invention can range from 0 to about 1 or above, typically above about 0.005, preferably about 0.01 to about 0.1, and most preferably from about 0.02 to about 0.05.

It has been found that AMS-1B crystalline borosilicate molecular sieve formed using the method of this invention in which such sieve is formed in a mixture containing a low water to silica ratio exhibits surprisingly high catalytic activity in hydrocarbon conversion such as in converting ethylbenzene. AMS-1B crystalline borosilicate compositions showing exceptional conversion activity can be prepared by crystallizing a mixture of an oxide of silicon, an oxide of boron, a alkylammonium compound and ethylenediamine such that the initial reactant molar ratios of water to silica range from, about 5 to about 25, preferably about 10 to about 22 and most preferably about 10 to about 15. In addition, preferable molar ratios for initial reactant silica to oxide of boron range from about 4 to about 150, more preferably about 5 to about 80 and most preferably about 5 to about 20. The molar ratio of ethylenediamine to silicon oxide used in the preparation of AMS-1B crystalline borosilicate according to this invention should be above about 0.05, typically below about 5, preferably about 0.1 to about 1.0, and most preferably about 0.2 to about 0.5. The molar ratio of alkylammonium template compound or precursor to silicon oxide useful in the preparation of this invention can range from 0 to about 1 or above, typically above about 0.005, preferably about 0.01 to about 0.1, and most preferably about 0.01 to about 0.1, and most preferably from about 0.02 to about 0.05.

It is noted that the preferable amount of alkylammonium template compound used in the preparation of this invention is substantially less than that required to produce AMS-1B conventionally using an alkali metal cation base. The decrease in use of such alkylammonium compound substantially lowers the cost of preparation.

The amount of alkylammonium template used in preparations of this invention generally is in inverse proportion to the amount of ethylenediamine used. If no alkylammonium compound is employed, preparations using ethylenediamine in a molar ratio to silica of above about 1 usually form highly crystalline borosilicate molecular sieves. At molar ratios below about 1 partially crystalline material is formed and at molar ratios below about 0.5 amorphous product is obtained. However, if an alkylammonium compound is included in a preparation using ethylenediamine in a molar ratio to silica less than about 1, crystalline AMS-1B borosilicate is formed. As the proportion of ethylenediamine is decreased, generally the proportion of alkylammonium compound may be increased. Nevertheless, in any preparation of this invention no added hydroxide, such as in the form of an alkali or alkaline earth metal hydroxide or ammonium hydroxide, is used, although insubstantial amounts may be present as impurities in starting reagents.

By regulation of the quantity of boron oxide (represented as $B_2O_3$) in the reaction mixture, it is possible to vary the $SiO_2/B_2O_3$ (silica/boria) molar ratio in the final product, although in many instances an excess of boron oxide is used in a preparation.

AMS-1B crystalline borosilicate molecular sieve generally can be characterized by the x-ray pattern listed in Table I and by the composition formula (in terms of oxides):

$$0.9 + 0.2\ M_{2/n}O : B_2O_3 : ySiO_2 : zH_2O$$

wherein M is at least one cation, n is the valence of the cation, y is between 4 and about 600 and z is between 0 and about 160.

TABLE I

| d-Spacing·Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong It has been found that preparations of AMS-1B by conventional techniques using sodium hydroxide sometimes contain searlesite as an impurity especially if the concentration of reactants in the crystallizing mixture is high. However, AMS-1B crystalline borosilicate can be prepared according to this invention using higher than conventional concentrations of reactants without producing searlesite. In addition, preparations at higher concentrations of reactants produce a crystalline borosilicate with increased activity in some hydrocarbon conversion processes. Further, higher reactant concentration preparations are economically more efficient.

More specifically, the material of the present invention is prepared by mixing in water (preferably distilled or deionized) ethylenediamine, a boron oxide source, and, optionally, an organic template compound such as tetra-n-propylammonium bromide. The order of addition usually is not critical although a typical procedure is to dissolve ethylenediamine and boric acid in water and then add the template compound. Generally, the silicon oxide compound is added with intensive mixing such as that performed in a Waring Blendor. The resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction system falls within the range of about 8 to about 12 and most preferably between about 9 and about 10.5. The pH depends on the concentration of ethylenediamine.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Since AMS-1B crystalline borosilicate prepared according to this invention requires no alkali metal cation and thus requires no ion exchange procedure before formulation into a catalytic composition, it is advantageous that the starting materials, such as silicon oxide and boron oxide, contain as little alkali metal ion contaminant as practicable.

Organic templates useful in preparing AMS-1B crystalline borosilicate include alkylammonium cations or precursors thereof such as tetraalkylammonium compounds. Useful organic templates include tetra-n-propylammonium bromide and tetra-n-propylammonium hydroxide.

In a more detailed description of a typical preparation of this invention, suitable quantities of ethylenediamine and boric acid ($H_3BO_3$) are dissolved in distilled or deionized water followed by addition of the organic template. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about two to about seven days, at a temperature is maintained below the decomposition temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 145° C. for about two to about four days. Samples to material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25–200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at about 145°–165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contract means. Preferred replacing cations are those which render the crystalline borosilicate catalytically active, especially for hydrocarbon conversion. Typical catalytically active ions include hydrogen, metal ions of Groups IB, IIA, IIB, IIIA, and VIII, and of manganese, vanadium, chromium, uranium, and rare earth elements.

Also, water soluble salts of catalytically active materials can be impregnated onto the crystalline borosilicate of this invention. Such catalytically active materials include hydrogen, metals of Groups IB, IIA, IIB, IIIA, IVB, VIB, VIIB, and VIII, and rare earth elements.

In another aspect of this invention a catalytically active material can be placed onto the borosilicate structure by incorporating such catalytically active material in the initial crystallization. Generally the same elements can be placed onto the sieve structure in this manner as can be ion exchanged or impregnated. Specific metal ions which can be incorporated in such manner include ions of Ni, Co, Mn, V, Ti, Cu, Zn, Mo and Zr.

Ion exchange and impregnation techniques are well known in the art. Typically, an aqueous solution of a cationic species is exchanged one or more times at about 25° to about 100° C. Impregnation of a catalytically active compound on the borosilicate or on a composition comprising the crystalline borosilicate suspended in and distributed throughout a matrix of a support material such as a porous refractory inorganic oxide such as alumina, often results in a suitable catalytic composition. A combination of ion exchange and impregnation can be used. Presence of sodium ion in a composition usually is detrimental to catalytic activity. AMS-1B-based catalyst compositions useful in xylene isomerization can be based on hydrogen form sieve or on that prepared by ion exchange with nickelous nitrate or by impregnation with ammonium molybdate.

The amount of catalytically active material placed on the AMS-1B borosilicate can vary from less than one weight percent to about thirty weight percent, typically from about 0.05 to about 25 weight percent, depending on the process use intended. The optimum amount can be determined easily by routine experimentation.

The AMS-1B crystalline borosilicate useful in this invention may be incorporated as a pure material in a catalyst or adsorbent, or may be admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, alumina sols, hydrated aluminas, clays such as bentonite or kaoline, or other binders well known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere up to 100 wt. % of the total composition. Catalytic compositions can contain about 0.1 wt. % to about 100 wt. % crystalline borosilicate material and typically contain about 2 wt. % to about 65 wt. % of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as aqueous ammonia. The resulting gel can be dried and calcined to form a composition in which the crystalline borosilicate and catalytically active metal compound are distributed throughout the matrix material.

Specific details of catalyst preparations are described in U.S. Pat. No. 4,268,420.

This invention is demonstrated but not limited by the following Examples and Comparative Runs.

EXAMPLES I-VI

A series of reaction mixtures prepared by dissolving ethylenediamine, boric acid, and tetra-n-propylammonium bromide (TPABr) in distilled water. While agitating this mixture in a Waring Blendor at maximum speed, a quantity of Ludox (40 wt. % $SiO_2$) was added quickly; agitation was continued for about ten minutes. The resulting mixture was charged to a stirred autoclave and digested at 145° C. After the mixture was crystallized, the resulting product was filtered, washed with distilled water, dried overnight at 130° C., and calcined at 530° C. for four hours preceded by a programmed preheating at a temperature increase of no more than 125° C./hour. The products were analyzed by x-ray diffraction and elemental analysis. Products characterized as AMS-1B had an x-ray diffraction pattern similar to that contained in Table I and elemental analysis showing incorporation of boron. Details of these preparations and analyses are summarized in Table II.

A catalyst composition was prepared by dispersing the above calcined sieve in PHF-alumina which is initially an acetic acid stabilized gamma alumina hydrosol containing about 9.8 wt. % $Al_2O_3$. Ten grams of calcined sieve were added and thoroughly mixed with 405 grams of alumina hydrosol. The mixture was gelled (solidified) with addition of 60 milliliters of concentrated aqueous ammonia. The resulting solid was dried overnight in a forced air oven at 130° C. The dried solid was program calcined at 530° C. with the program as described above. The calcined solid was crushed and sized to 18 to 40 mesh (U.S. Sieve Series). Five grams of the 18-40 mesh catalyst were placed in a micro aromatics test unit having a 0.5 inch inside diameter tubular reactor and preconditioned for two hours at 399° C. and 165 psig pressure with 0.3 SCF per hour flow of hydrogen. Xylene isomerization test results are shown in Table III.

TABLE II

| | Examples | | | | | |
|---|---|---|---|---|---|---|
| | I | II | III | IV | V | VI |
| Reagents (grams) | | | | | | |
| Water | 2,000 | 6,000 | 2,000 | 2,000 | 9,000 | 7,800 |
| Ethylenediamine | 79 | 120 | 40 | 132 | 600 | 433 |
| Boric Acid | 102 | 306.6 | 102.7 | 102.7 | 460 | 400 |
| Tetra-n-propyl-ammonium Bromide | 27 | 80 | 81 | 81 | 120 | 104 |
| Ludox (HS-40, 40 wt. % $SiO_2$) | 666 | 2,000 | 666 | 666 | 3,000 | 2,600[1] |
| Mole Ratios of Reagents | | | | | | |
| $SiO_2/B_2O_3$ | 5.38 | 5.38 | 5.38 | 5.38 | 5.38 | 5.38 |
| $H_2O/SiO_2$ | 30 | 30 | 30 | 30 | 30 | 30 |
| Ethylenediamine/$SiO_2$ | 0.30 | 0.15 | 0.15 | 0.45 | 0.45 | 0.375 |
| TPABr/$SiO_2$ | 0.023 | 0.023 | 0.069 | 0.069 | 0.023 | 0.023 |
| Crystallization Conditions | | | | | | |
| Time (days) | 6 | 3 | 4 | 7 | 6 | 3 |
| Temperature (°C.) | 145 | 165 | 145 | 145 | 145 | 145 |
| Initial pH | 9.8 | 8.8 | 8.8 | 10.0 | 10.0 | 9.8 |
| Elemental Analysis (wt. %) | | | | | | |
| $SiO_2$ | 93.5 | 94.7 | 92.2 | 95.7 | 93.2 | 89.8 |
| B | 0.82 | — | — | — | 0.86 | 0.88 |
| Na | 0.01 | 0.031 | 0.030 | 0.02 | 0.005 | 0.01 |

[1]Ludox AS-40 used which contains 40 wt. % $SiO_2$ and 0.08 wt. % $Na_2O$; Ludox HS-40 contains about 0.4 wt. % $Na_2O$.

TABLE III

| | Test Runs from Examples | | | | | | | | | | | |
|---|---|---|---|---|---|---|---|---|---|---|---|---|
| | I | | II[2] | | III | | IV | | V | | VI | |
| Conditions | | | | | | | | | | | | |
| Reactor Temp. (°C.) | 399 | | 399 | | 399 | | 399 | | 399 | | 399 | |
| Reactor Pressure (psig) | 165 | | 165 | | 165 | | 165 | | 165 | | 165 | |
| Space Velocity (WHSV, $hr^{-1}$) | 7.2 | | 4.9 | | 6.9 | | 6.9 | | 5.0 | | 6.9 | |
| Hydrogen/hydrocarbon (molar ratio) | 4.9 | | 5.7 | | 5.1 | | 5.0 | | 5.0 | | 5.0 | |
| Components (wt. %) | Feed | | Feed | | Feed | | Feed | | Feed | | Feed | |
| Paraffins and Naphthenes | 0.24 | 0.27 | 0.00 | 0.22 | 0.01 | 0.43 | 0.24 | 0.18 | 0.00 | 0.26 | 0.24 | 0.29 |
| Benzene | 0.03 | 2.37 | 0.03 | 1.39 | 0.07 | 1.26 | 0.03 | 0.94 | 0.03 | 1.96 | 0.03 | 2.43 |

TABLE III-continued

|  | Test Runs from Examples | | | | | | | | | | | |
|---|---|---|---|---|---|---|---|---|---|---|---|---|
|  | I | | II[(2)] | | III | | IV | | V | | VI | |
| Toluene | 0.07 | 0.51 | 0.06 | 0.35 | 0.07 | 0.41 | 0.07 | 0.33 | 0.06 | 0.55 | 0.07 | 0.54 |
| Ethylbenzene | 13.78 | 9.85 | 14.30 | 12.20 | 14.59 | 12.69 | 13.78 | 12.47 | 14.30 | 10.85 | 13.78 | 9.73 |
| p-Xylene | 10.16 | 20.07 | 8.98 | 16.84 | 8.86 | 16.25 | 10.16 | 20.19 | 8.98 | 16.88 | 10.16 | 20.01 |
| m-Xylene | 52.67 | 44.11 | 53.25 | 46.24 | 52.50 | 46.41 | 52.67 | 44.50 | 53.25 | 46.18 | 52.67 | 44.19 |
| o-Xylene | 22.98 | 19.42 | 23.31 | 20.79 | 23.84 | 21.10 | 22.98 | 20.17 | 23.31 | 20.34 | 22.98 | 19.39 |
| $C_{9+}$ | 0.07 | 3.39 | 0.07 | 1.97 | 0.08 | 1.46 | 0.07 | 1.22 | 0.07 | 2.97 | 0.07 | 3.42 |
| Results[(1)] | | | | | | | | | | | | |
| PATE - p-Xylene | | 104.1 | | 73.5 | | 68.6 | | 102.3 | | 74.8 | | 103.5 |
| Ethylbenzene conversion (%) | | 28.5 | | 14.7 | | 13.0 | | 9.5 | | 24.1 | | 29.4 |

[(1)]PATE = Percent Approach to Theoretical Equilibrium
[(2)]Test run on 20 grams of catalyst in a Berty reactor. Lower PATE appears to be a characteristic of this reactor.

EXAMPLE VII

This example demonstrates crystallizing a crystalline borosilicate together with a nickel salt according to the method of this invention. A solution of 620 milliliters of ethylenediamine, 460 grams of boric acid, 120 grams of TPABr and 90 grams of $Ni(CH_3COO)_2 \cdot 4H_2O$ in 9,000 milliliters of water was placed in a five-gallon autoclave followed by 3,000 grams of Ludox HS-40. The autoclave was closed and maintained at 145° C. for seven days. The resulting crystalline product after washing, drying and calcination had a 1.26 wt. % nickel content. A 20% sieve/80% $Al_2O_3$ catalyst composition was formed and tested for xylene isomerization and ethylbenzene conversion. The results showed a 37% ethylbenzene conversion and grater than 100% p-xylene approach to theoretical equilibrium.

EXAMPLE VIII

An AMS-1B crystalline borosilicate was prepared using increased concentrations of reactants with respect to the water diluent. The molecular sieve was prepared in a manner similar to that described in Examples I–VI except that proportionately less water was used. Details of the preparation and analyses are shown in Table IV. A catalyst composition was prepared by dispersing 10 grams of calcined sieve as described above in 405 grams of PHF-alumina hydrosol. The mixture was gelled with 20 milliliters of concentrated aqueous ammonia. The resulting solid was dried overnight in a forced air oven at 130° C. and then program calcined at 530° C. for twelve hours preceded by a temperature increase of 125° C./hour. The calcined solid was crushed and sized to 18–40 mesh (U.S. Sieve Series) and five grams of such 18–40 mesh catalyst were placed into a micro aromatics test unit having a 0.5-inch inside diameter tubular reactor and preconditioned for two hours at 399° C. an 165 psig pressure with 0.3 SCF per hour flow of hydrogen. Xylene isomerization test results are shown in Table V.

TABLE IV

|  | Example VIII |
|---|---|
| Reagents (grams) | |
| Water | 5,400 |
| Ethylenediamine | 720 |
| Boric Acid | 920 |
| Tetra-n-propylammonium Bromide | 240 |
| Ludox (HS-40, 40 wt. % $SiO_2$) | 6,000 |
| Mole Ratios of Reagents | |
| $SiO_2/B_2O_3$ | 5.38 |
| $H_2O/SiO_2$ | 12.5 |
| Ethylenediamine/$SiO_2$ | 0.30 |
| TPABr/$SiO_2$ | 0.023 |
| Crystallization Conditions | |
| Time (days) | 7 |
| Temperature (°C.) | 145 |
| Initial pH | 9.8 |
| Elemental Analysis (wt. %) | |
| B | 1.09 |

TABLE V

|  | Test Run for Example VIII | |
|---|---|---|
| Conditions | | |
| Reactor Temp. (°C.) | | 399 |
| Reactor Pressure (psig) | | 165 |
| Space Velocity (WHSV, $hr^{-1}$) | | 6.8 |
| Hydrogen/hydrocarbon (molar ratio) | | 4.6 |
| Components (wt. %) | Feed | |
| Paraffins and Naphthenes | 0.00 | 0.02 |
| Benzene | 0.05 | 3.51 |
| Toluene | 0.05 | 0.84 |
| Ethylbenzene | 13.33 | 7.63 |
| p-Xylene | 10.05 | 19.96 |
| m-Xylene | 53.55 | 43.24 |
| o-Xylene | 22.93 | 19.21 |
| $C_{9+}$ | 0.06 | 5.60 |
| Results[(1)] | | |
| PATE - p-Xylene | | 105.8 |
| Ethylbenzene conversion (%) | | 42.7 |

[(1)]PATE = Percent Approach to Theoretical Equilibrium

EXAMPLES IX–XII

A series of experiments was performed using ethylenediamine with no added alkylammonium salt. Preparations were attempted in a manner similar to that described in Examples I–VI except that no tetra-n-propyl ammonium bromide was used. Details of the preparation and analyses are shown in Table VI.

TABLE VI

| | Examples (Run) | | | | |
|---|---|---|---|---|---|
| | IX | X | XI | XII | A |
| Reagents (grams) | | | | | |
| Water | 850 | 2,000 | 2,000 | 2,000 | 2,000 |
| Ethylenediamine | 972 | 495 | 371 | 248 | 79 |
| Boric Acid | 10 | 102 | 460 | 400 | 102 |
| Ludox (HS-40, 40 wt. % $SiO_2$) | 400 | 666 | 666 | 666 | 666 |
| Mole Ratios of Reagents | | | | | |
| $SiO_2/B_2O_3$ | 16.67 | 5.38 | 5.38 | 0.186 | 0.186 |
| $H_2O/SiO_2$ | 22.7 | 30 | 30 | 30 | 30 |
| Ethylenediamine/$SiO_2$ | 3.65 | 1.86 | 1.39 | 0.93 | 0.30 |
| Crystallization Conditions | | | | | |
| Time (days) | 5 | 5 | 5 | 5 | 5 |
| Temperature (°C.) | 150 | 150 | 150 | 150 | 150 |
| AMS-1B (% crystallinity) | 81 | 82 | >80 | 43 | 0 |
| Elemental Analysis (wt. %) | | | | | |
| B | 0.92 | — | — | — | — |
| Na | — | — | — | — | — |

EXAMPLES XIII-XIV

A series of preparations of AMS-1B crystalline borosilicate was conducted according to this invention to show the substantial increase hydrocarbon conversion catalytic activity of AMS-1B material made using increased concentrations of reactants with respect to water. The AMS-1B crystalline borosilicate of Example XIII was prepared using ethylenediamine with no added metal hydroxide and with a low water to silica molar ratio. The material prepared in Example XIII is similar to that prepared in Example VIII. The AMS-1B of Example XIV was prepared in a manner similar to that described in Examples I-VII using a higher water to silica molar ratio. Comparative Run B was prepared using sodium hydroxide as the base with no ethylenediamine.

Xylene isomerization/ethylbenzene conversion tests using catalysts prepared from the materials of Examples XIII and XIV and Comparative Run B show the catalyst prepared from the Example XIII material to have a substantially higher ethylbenzene conversion activity as compared to similarly-formulated catalysts made from the other materials.

The AMS-1B crystalline borosilicate molecular sieve of Example XIII was prepared by mixing in an autoclave distilled water, ethylenediamine, boric acid, tetra-n-propylammonium bromide and Ludox HS-40 silica sol (40 wt. % solids). The resulting mixture was digested for four days at 145° C., after which time the product was washed thoroughly with distilled water, dried at 130° C. for 16 hours and calcined at 535° C. for 12 hours after a programmed rate of heating of 125° C./hour for four hours. The resulting molecular sieve had particle sizes of 0.1-0.5 micrometers. Mole ratios of reagents were $SiO_2/B_2O_3=5.38$; $H_2O/SiO_2=15$; ethylenediamine/$SiO_2=0.30$; TPABr/$SiO_2=0.023$. The AMS-1B crystalline borosilicate of Example XIII had a boron content of 0.85 wt. %.

Catalyst compositions were prepared by dispersing the above-prepared sieve in 1667 grams of PHF gamma alumina hydrosol (9.6 wt. % solids) and gelling with 80 milliliters of concentrated aqueous ammonia (28 wt. % $NH_3$). Several catalysts were prepared using different sieve/alumina matrix weight ratios. The following amounts of sieve were used for the corresponding sieve/alumina matrix weight ratios: 20/80=40.0 grams; 30/70=68.6 grams; 35/65=86.2 grams; 40/60=106.7 grams; 45/55=130.9 grams; and 55/45=195.6 grams. The gelled solid was dried overnight in a forced air oven at 130° C., ground to 18-40 mesh (U.S. Sieve Series), and then calcined at 537° C. for 12 hours preceded by a temperature increase of 125° C./hour. Five to ten grams of the resulting calcined catalyst was placed into an micro aromatics test unit having a 0.5-inch inside diameter tubular reactor and preconditioned for two hours at 371° C. and 250 psig pressure with 0.3 SCF per hour hydrogen flow. Xylene isomerization/ethylbenzene conversion test results are shown in Table VII.

AMS-1B crystalline borosilicate molecular sieve of Example XIV was prepared in a manner similar to that described in Example I using Ludox HS-40 (40 wt. % $SiO_2$), tetrapropylammonium bromide, boric acid, ethylenediamine and water such that the molar ratios of reactants were $SiO_2/B_2O_3=5.38$; $H_2O/SiO_2=30$; ethylenediamine/$SiO_2=0.30$ and TPABr/$SiO_2=0.023$. The reactant mixture was digested at 132-136° C. for 4.5 days after which time the resulting solids were washed thoroughly with distilled water dried at 130° C. and calcined at 530° C. The resulting AMS-1B crystalline borosilicate molecular sieve had particle sizes of 0.2-2 micrometers and a boron content of 0.85 wt. %. Catalyst compositions with various sieve/alumina matrix weight ratios were prepared as described for Example XIII.

For a 20/80 sieve/alumina matrix catalyst, 417 grams of PHF gamma alumina sol (9.8 wt. % solids), 10.0 grams of sieve and 60 milliliters of concentrated aqueous ammonia (28 wt. % $NH_3$) gelling agent were used; for a 30/70 silica/matrix catalyst, 1215.9 grams of alumina sol, 51.39 grams of sieve and 120 milliliters of aqueous ammonia were used; for a 35/65 catalyst 1215.9 grams of alumina sol 64.56 grams of sieve and 60 milliliters of aqueous ammonia were used; and for a 40/60 catalyst 405.3 grams of alumina sol, 26.67 grams of sieve and 60 milliliters of aqueous ammonia were used. These catalyst compositions were tested for xylene isomerization/ethylbenzene conversion as described for Example XIII and the results shown in Table VIII.

AMS-1B crystalline borosilicate molecular sieve of Comparative Run B was prepared by digesting a mixture of water, boric acid, sodium hydroxide, tetrapropylammonium bromide and Ludox HS-40 (40 wt. % SiO$_2$) for 2.5 days at 145° C. The molar ratios of reactants were: SiO$_2$/B$_2$O$_3$=5.06; H$_2$O/SiO$_2$=30.5; NaOH/SiO$_2$=0.42; and TPABr/SiO$_2$=0.14. Resulting solids were washed with water, dried and calcined. The calcined sieve then was exchanged twice with an ammonium acetate solution at 90° C. for two hours. Two grams of ammonium acetate in ten grams of water per gram of sieve were used in the exchanges. The resulting exchanged sieve was dried and calcined and then formulated into catalysts incorporated into a gamma alumina matrix as described above for Example XIII. The AMS-1B crystalline borosilicate of Run B had particle sizes of 0.1-0.5 micrometers and a boron content of 0.5 wt. %. The quantities of PHF alumina sol (9.7 wt. % solids), sieve and aqueous ammonia for various sieve/alumina matrix weight ratios are: 20/80-2060 grams alumina sol, 50 grams of sieve and 400 milliliters aqueous ammonia; 30/70-1500 grams alumina sol, 62.3 grams of sieve and 218 milliliters acqueous ammonia; 35/65-1675.3 grams alumina sol, 87.5 grams of sieve and 325 milliliters of aqueous ammonia; 40/60-1546.4 grams alumina sol; 100 grams of sieve and 300 milliliters of aqueous ammonia. These catalyst compositions were tested for xylene isomerization/ethylbenzene conversion as described for Example XIII and the results are shown in Table IX.

The data show that catalylic materials formulated from AMS-1B crystalline borosilicate molecular sieve of Example XIII are significantly more active for ethylbenzene conversion than similarly formulated materials prepared as in Example XIV and Run B.

TABLE VII

| | Test Runs from Example XIII | | | | | | | | | | | |
|---|---|---|---|---|---|---|---|---|---|---|---|---|
| | Sieve/Alumina Matrix (wt. ratio) | | | | | | | | | | | |
| | 20/80 | | 30/70 | | 35/65 | | 40/60 | | 45/55 | | 55/45 | |
| Conditions | | | | | | | | | | | | |
| Reactor Temp. (°C.) | 372 | | 371 | | 371 | | 371 | | 371 | | 372 | |
| Reactor Pressure (psig) | 250 | | 250 | | 250 | | 250 | | 250 | | 250 | |
| Space Velocity (WHSV, hr$^{-1}$) | 6.0 | | 6.1 | | 6.0 | | 6.0 | | 6.0 | | 6.0 | |
| Hydrogen/hydrocarbon (molar ratio) | 2.1 | | 1.9 | | 2.0 | | 2.0 | | 2.0 | | 2.0 | |
| Components (wt. %) | Feed | | Feed | | Feed | | Feed | | Feed | | Feed | |
| Paraffins and Naphthenes | 0.01 | 0.08 | 0 | 0.02 | 0.01 | 0.14 | 0.01 | 0.19 | 0 | 0.03 | 0.01 | 0.16 |
| Benzene | 0.04 | 2.03 | 0.05 | 2.43 | 0.04 | 3.39 | 0.04 | 3.94 | 0.05 | 3.14 | 0.04 | 3.08 |
| Toluene | 0.05 | 0.56 | 0.05 | 0.80 | 0.05 | 0.96 | 0.05 | 1.21 | 0.05 | 1.07 | 0.05 | 0.81 |
| Ethylbenzene | 13.90 | 10.35 | 13.33 | 8.89 | 13.90 | 8.24 | 13.90 | 7.28 | 13.33 | 7.68 | 13.90 | 8.67 |
| p-Xylene | 10.32 | 20.22 | 10.05 | 20.11 | 10.32 | 19.67 | 10.32 | 19.36 | 10.05 | 19.79 | 10.32 | 19.92 |
| m-Xylene | 52.90 | 44.06 | 53.55 | 43.85 | 52.90 | 42.94 | 52.90 | 42.58 | 53.55 | 43.32 | 52.90 | 43.36 |
| o-Xylene | 22.71 | 19.03 | 22.93 | 19.05 | 22.71 | 18.61 | 22.71 | 18.25 | 22.93 | 18.74 | 22.71 | 18.83 |
| C$_{9+}$ | 0.07 | 3.67 | 0.05 | 4.85 | 0.07 | 6.05 | 0.07 | 7.19 | 0.05 | 6.23 | 0.07 | 5.17 |
| Results[1] | | | | | | | | | | | | |
| PATE - p-Xylene | | 105.6 | | 105.0 | | 105.1 | | 104.5 | | 104.5 | | 105.5 |
| Ethylbenzene conversion (%) | | 25.6 | | 33.3 | | 40.7 | | 47.6 | | 42.5 | | 37.7 |
| Xylene Loss (wt. %) | | 3.06 | | 4.27 | | 5.43 | | 6.72 | | 5.76 | | 4.48 |

[1]PATE = Percent Approach to Theoretical Equilibrium

TABLE VIII

| | Test Runs from Example XIV | | | | | | | |
|---|---|---|---|---|---|---|---|---|
| | Sieve/Alumina Matrix (wt. ratio) | | | | | | | |
| | 35/65 | | 40/60 | | 20/80 | | 30/70 | |
| Conditions | | | | | | | | |
| Reactor Temp. (°C.) | 372 | | 371 | | 372 | | 372 | |
| Reactor Pressure (psig) | 250 | | 250 | | 250 | | 250 | |
| Space Velocity (WHSV, hr$^{-1}$) | 6.0 | | 5.9 | | 6.1 | | 6.3 | |
| Hydrogen/hydrocarbon (molar ratio) | 2.0 | | 2.1 | | 2.2 | | 1.9 | |
| Components (wt. %) | Feed | | Feed | | Feed | | Feed | |
| Paraffins and Naphthenes | 0.01 | 0.09 | 0 | 0.02 | 0 | 0.02 | 0 | 0.03 |
| Benzene | 0.04 | 2.77 | 0.04 | 1.88 | 0.05 | 1.67 | 0.05 | 2.23 |
| Toluene | 0.05 | 0.80 | 0.06 | 0.77 | 0.05 | 0.59 | 0.05 | 0.95 |
| Ethylbenzene | 13.90 | 9.12 | 14.01 | 10.51 | 13.33 | 10.19 | 13.33 | 9.34 |
| p-Xylene | 10.32 | 20.00 | 10.36 | 20.09 | 10.05 | 20.42 | 10.05 | 20.09 |
| m-Xylene | 52.90 | 43.49 | 52.73 | 44.00 | 53.55 | 44.53 | 53.55 | 43.68 |
| o-Xylene | 22.71 | 18.88 | 22.74 | 18.89 | 22.93 | 19.31 | 22.93 | 19.02 |
| C$_{9+}$ | 0.07 | 4.86 | 0.06 | 3.85 | 0.05 | 3.28 | 0.06 | 4.66 |
| Results[1] | | | | | | | | |
| PATE - p-Xylene | | 105.6 | | 105.1 | | 105.1 | | 105.3 |
| Ethylbenzene conversion (%) | | 34.4 | | 25.0 | | 23.6 | | 29.9 |

TABLE VIII-continued

Test Runs from Example XIV

| | Sieve/Alumina Matrix (wt. ratio) | | | |
|---|---|---|---|---|
| | 35/65 | 40/60 | 20/80 | 30/70 |
| Xylene Loss (wt. %) | 4.16 | 3.41 | 2.81 | 4.31 |

[1]PATE = Percent Approach to Theoretical Equilibrium

TABLE IX

Test Runs from Run B

| | Sieve/Alumina Matrix (wt. ratio) | | | | | | | |
|---|---|---|---|---|---|---|---|---|
| | 35/65 | | 40/60 | | 20/80 | | 30/70 | |
| Conditions | | | | | | | | |
| Reactor Temp. (°C.) | 373 | | 373 | | 373 | | 371 | |
| Reactor Pressure (psig) | 250 | | 250 | | 250 | | 250 | |
| Space Velocity (WHSV, hr$^{-1}$) | 6.0 | | 6.0 | | 6.0 | | 6.0 | |
| Hydrogen/hydrocarbon (molar ratio) | 2.0 | | 2.0 | | 2.0 | | 1.8 | |
| Components (wt. %) | Feed | | Feed | | Feed | | Feed | |
| Paraffins and Naphthenes | 0 | 0.01 | 0 | 0.07 | 0 | 0 | 1.16 | 1.15 |
| Benzene | 0.03 | 2.37 | 0.03 | 2.55 | 0.03 | 1.33 | 0 | 2.27 |
| Toluene | 0.05 | 0.58 | 0.05 | 0.62 | 0.05 | 0.32 | 0.85 | 1.68 |
| Ethylbenzene | 14.32 | 10.22 | 14.32 | 10.00 | 14.32 | 12.17 | 14.65 | 10.97 |
| p-Xylene | 10.14 | 19.94 | 10.14 | 19.86 | 10.14 | 20.41 | 7.79 | 18.30 |
| m-Xylene | 52.24 | 43.55 | 52.24 | 43.29 | 52.24 | 44.08 | 49.74 | 40.00 |
| o-Xylene | 23.18 | 18.94 | 23.18 | 18.88 | 23.18 | 19.24 | 21.13 | 16.90 |
| C$_{9+}$ | 0.04 | 4.41 | 0.04 | 4.74 | 0.04 | 2.45 | 4.67 | 8.73 |
| Results[1] | | | | | | | | |
| PATE - p-Xylene | | 104.8 | | 105.0 | | 106.3 | | 105.2 |
| Ethylbenzene conversion (%) | | 28.6 | | 30.2 | | 15.0 | | 25.1 |
| Xylene Loss (wt. %) | | 3.49 | | 3.84 | | 1.84 | | 4.51 |

[1]PATE = Percent Approach to Theoretical Equilibrium

What is claimed is:

1. A method to prepare AMS-1B crystalline borosilicate molecular sieve comprising reacting under crystallization conditions, in substantial absence of a metal or ammonium hydroxide, an aqueous mixture containing an oxide of silicon in a molar ratio of water to oxide of silicon of between about 5 to about 15, an oxide of boron, ethylenediamine in a molar ratio to silica of above about 0.05, and, optionally, an alkylammonium cation or precursor of an alkylammonium cation.

2. The method of claim 1 wherein the alkylammonium cation is tetra-n-propylammonium cation.

3. The method of claim 1 wherein the molar ratio of alkylammonium cation or precursor of an alkylammonium cation to silica is between about 0.005 and about 1.0, the molar ratio of silica to oxide of boron is about 2 to about 400.

4. The method of claim 3 wherein the alkylammonium cation is tetra-n-propylammonium cation.

5. The method of claim 1, 2, 3 or 4 wherein the source for oxide of boron is boric acid.

6. The method of claim 2 wherein the molar ratio of tetra-n-proplyammonium cation or precursor to silica is about 0.01 to about 0.1, the molar ratio of ethylenediamine to silica is about 0.1 to about 1.0, the molar ratio of silica to oxide of boron is about 5 to about 80.

7. The method of claim 6 wherein the molar ratio of ethylenediamine to silica is about 0.2 to about 0.5, the molar ratio of tetra-n-propylammonium cation or precursor to silica is about 0.02 to about 0.05.

8. The method of claim 6 wherein the molar ratio of water to silica is about 10 to 15.

9. The method of claim 1 wherein a catalytically active material is placed on the borosilicate.

10. The method of claim 1 wherein the crystallizing mixture is maintained at about 125° C. to about 200° C. for about one to about ten days.

11. The method of claim 1 wherein the molecular sieve is incorporated within a suitable matrix material.

12. The method of claim 11 wherein the matrix material is silica, silica-alumina or alumina.

13. The method of claim 1 wherein ions of nickel, cobalt, manganese, vanadium, titanium, copper, zinc, molybdenum or zirconium are incorporated within the crystallizing mixture.

14. A method to prepare AMS-1B crystalline borosilicate molecular sieve comprising reacting under crystallization conditions, in substantial absence of a metal or amonium hydroxide, an aqueous mixture containing an oxide of silica, an oxide of boron, ethylenediamine in a molar ratio to silica of above about 0.05, and, optionally, an alkylammonium cation or precursor of an alkylammonium cation; wherein the molar ratio silica to oxide of boron is about 4 to about 150 and the molar ratio of water to silica is about 5 to about 15.

15. The method of claim 14 wherein the molar ratio of water to silica is about 10 to about 15.

16. The method of claim 14 or 15 wherein the molar ratio of alkylammonium cation or precursor to silica is about 0.01 to about 0.1 and the molar ratio of ethylenediamine to silica is about 0.1 to about 1.0.

17. The method of claim 14 wherein the alkylammonium cation is tetra-n-prooylammonium cation.

18. The method of claim 15 wherein the alkylammonium cation is tetra-n-propylammonium cation.

19. The method of claim 18 wherein the molar ratio of tetra-n-propylammonium cation to silica is about 0.01 to about 0.1, the molar ratio of silica to oxide of boron is about 5 to about 80, and the molar ratio of ethylenediamine to silica is about 0.1 to about 1.0.

20. The method of claim 18 wherein the molar ratio of tetra-n-propylammonium cation to silica is about 0.02 to about 0.05, the molar ratio of silica to oxide of boron is about 5 to about 20 and the molar ratio of ethylenediamine to silica is about 0.2 to about 0.5.

21. The method of claim 17, 18, 19 or 20 wherein the source for oxide of boron is boric acid and the source for tetra-n-propylammonium cation is tetra-npropylammonium bromide.

* * * * *

UNITED STATES PATENT AND TRADEMARK OFFICE
CERTIFICATE OF CORRECTION

PATENT NO. : 5,053,211
DATED : October 1, 1991
INVENTOR(S) : Muin S. Haddad

It is certified that error appears in the above-indentified patent and that said Letters Patent is hereby corrected as shown below:

On the title page, item [54] and column 1, line 2, "18" should read --1B--.

Signed and Sealed this

Twenty-first Day of June, 1994

Attest:

BRUCE LEHMAN

Attesting Officer     Commissioner of Patents and Trademarks